(12) United States Patent
Sabourin (10) Patent No.: US 9,173,726 B2
(45) Date of Patent: Nov. 3, 2015

(54) ILLUMINATED INTRA-ORAL DELIVERY DEVICE

(71) Applicant: Christopher R. Sabourin, Clovis, CA (US)

(72) Inventor: Christopher R. Sabourin, Clovis, CA (US)

(*) Notice: Subject to any disclaimer, the term of this patent is extended or adjusted under 35 U.S.C. 154(b) by 0 days.

(21) Appl. No.: 14/135,354

(22) Filed: Dec. 19, 2013

(65) Prior Publication Data

US 2015/0024335 A1  Jan. 22, 2015

Related U.S. Application Data

(60) Provisional application No. 61/847,802, filed on Jul. 18, 2013.

(51) Int. Cl.
*A61C 19/08* (2006.01)
*A61C 1/08* (2006.01)

(52) U.S. Cl.
CPC ............ *A61C 19/08* (2013.01); *A61C 1/088* (2013.01)

(58) Field of Classification Search
CPC .. A61C 1/088; A61C 17/0202; A61C 19/004; A61C 5/062; A61M 2205/587
USPC ................................. 604/187, 218
See application file for complete search history.

(56) References Cited

U.S. PATENT DOCUMENTS

| | | | |
|---|---|---|---|
| 3,556,099 A * | 1/1971 | Knight et al. | 604/232 |
| 4,311,138 A | 1/1982 | Sugarman | |
| 4,551,129 A | 11/1985 | Coleman et al. | |
| 4,648,838 A | 3/1987 | Schlachter | |
| 4,886,455 A | 12/1989 | Löhn | |
| 5,030,207 A | 7/1991 | Mersch et al. | |
| 5,137,518 A | 8/1992 | Mersch | |
| 5,271,734 A | 12/1993 | Takeuchi | |
| 5,586,976 A | 12/1996 | Coutoumanos | |
| 5,833,456 A | 11/1998 | Davis et al. | |
| 5,868,563 A * | 2/1999 | Davis et al. | 433/29 |
| 5,899,692 A | 5/1999 | Davis et al. | |
| 6,305,934 B1 | 10/2001 | Hatley, Jr. | |
| 6,406,293 B1 | 6/2002 | Burstein | |

(Continued)

FOREIGN PATENT DOCUMENTS

WO  2012/139155 A1  10/2012
WO  2012/153295 A2  11/2012

OTHER PUBLICATIONS

Dentistry IQ, "Minimizing injection pain and stress," retrieved on Oct. 8, 2014, from http://web.archive.org/web/20120618111424/http://www.dentistryiq.com/articles/201 0/02/minimizing-injection-pain-and-stress.html, DIQ Article Archives, Jun. 18, 2012. 7 pages.

(Continued)

*Primary Examiner* — Aarti B Berdichevsky
(74) *Attorney, Agent, or Firm* — Seed IP Law Group PLLC (57) ABSTRACT

A medical syringe with a light source mounted on a distal end of the syringe to provide illumination of an injection site, a battery pack receiver configured to receive a battery pack with magnetic attraction a proximal end of the syringe, and a control circuit that is configured to illuminate the light source when the control circuit detects movement of the syringe and disconnects the battery from the light source either after a fixed period of time or after motion of the syringe ceases. Ideally the light source is a disc-shaped array of LED lights. The syringe is constructed of materials that can be sterilized.

17 Claims, 12 Drawing Sheets

(56) References Cited

U.S. PATENT DOCUMENTS

| | | |
|---|---|---|
| 6,569,089 B1 | 5/2003 | Covington et al. |
| 7,549,977 B2 | 6/2009 | Schriver et al. |
| 7,632,004 B2 | 12/2009 | Chien |
| 7,682,345 B2 | 3/2010 | Savage |
| 7,896,838 B2 | 3/2011 | Devega |
| 8,162,906 B2 | 4/2012 | Terrill et al. |
| 8,403,843 B2 | 3/2013 | Bruto Da Costa |
| 2005/0080384 A1 | 4/2005 | Green, Jr. |
| 2006/0069314 A1 | 3/2006 | Farr |
| 2006/0124862 A1 | 6/2006 | Rodriquez |
| 2007/0055195 A1 | 3/2007 | Browne |
| 2008/0014548 A1* | 1/2008 | Paxton ............... 433/90 |
| 2008/0097378 A1 | 4/2008 | Zuckerman |
| 2008/0182222 A1* | 7/2008 | Li ............... 433/29 |
| 2008/0195048 A1 | 8/2008 | Niehoff |
| 2009/0177155 A1 | 7/2009 | Schriver et al. |
| 2009/0247956 A1 | 10/2009 | Devega |
| 2010/0190129 A1 | 7/2010 | Paz |
| 2010/0256486 A1 | 10/2010 | Savage |
| 2010/0286659 A1 | 11/2010 | Terrill et al. |
| 2011/0196312 A1* | 8/2011 | DeVega ............... 604/218 |
| 2011/0256501 A1 | 10/2011 | Lampert |
| 2012/0040305 A1* | 2/2012 | Karazivan et al. ............... 433/29 |
| 2012/0098465 A1* | 4/2012 | Rothschild ............... 315/360 |
| 2012/0251386 A1 | 10/2012 | Wootton et al. |
| 2013/0072757 A1* | 3/2013 | Mcgrath et al. ............... 600/188 |

OTHER PUBLICATIONS

International Search Report, mailed Nov. 7, 2014, for International Application No. PCT/US2014/046914, 2 pages.

* cited by examiner

ILLUMINATED INTRA-ORAL DELIVERY DEVICE

BACKGROUND

1. Technical Field

The present disclosure is directed to the provision of light at an oral injection site and, more particularly, to an automated lighting system adapted for use with syringes.

2. Description of the Related Art

In some health care fields, it is sometimes necessary to perform fluid injections, irrigations, and withdrawals in locations that are dimly lit. In particular, dentists frequently perform anesthetic injections near the back of a patient's mouth. Because of the small opening of the mouth, it can be difficult to see an injection site inside the mouth. The space constraints of a patient's mouth also make it difficult to align an external light source to the injection site.

One proposed solution has been to create a syringe that utilizes a light source at the needle end of the syringe in order to allow for better illumination of an injection site. Some of these syringe designs include light sources that are located remotely from the syringe, but use fiber optics to channel the light to a distal end of the syringe. Other proposed solutions have seen the light source built into the syringe, generally near the distal end of the syringe.

However, these syringes fail to provide a medical practitioner with a practical means for illuminating an injection site. In nearly all medical fields sterilization and hygiene is an extremely important aspect of all procedures, especially injection or irrigation. In addition, a practitioner may have several tasks to carry out in order to properly perform the injection, and these tasks may prevent them from operating or focusing on additional devices. A practitioner therefore may not have the ability or time to control electronics or other additional devices while using the syringe. In addition, most of these prior designs cannot be sterilized without requiring disassembly and then reassembly prior to the next use. Moreover, portable sources of power, such as batteries, require partial disassembly to replace the batteries.

What is needed is an apparatus that can provide illumination of injection sites without burdening the practitioner with additional tasks or devices to operate, that provides automation in its use, can be easily sterilized, and enables quick removal and replacement of the battery.

BRIEF SUMMARY

In accordance with one aspect of the present disclosure, an illuminated syringe for use in medical and dental fields is presented. The illuminated syringe utilizes a light source coupled to a battery through a control circuit to illuminate an injection site when the control circuit senses motion, such as when the syringe is picked up.

In accordance with another aspect of the present disclosure, an apparatus is provided that includes a syringe having a barrel with a proximal end and a distal end, a plunger mounted in the barrel and longitudinally slidable through the proximal end of the barrel, a light source mounted on the distal end of the barrel, a battery pack receiver on the proximal end of the barrel and configured to be electrically coupled to the light source, and a control circuit electrically coupled to the battery pack receiver and the light source and configured to detect motion of the syringe and to electrically couple the battery pack receiver and the light source in response to detecting motion of the syringe.

In accordance with another aspect of the present disclosure, the syringe includes a battery pack configured to be removably mounted to the battery pack receiver by magnetic attraction between the battery pack and the battery pack receiver.

In accordance with yet another aspect of the present disclosure, a first magnet is provided in the battery pack receiver and a second magnet is provided in the battery pack configured to be magnetically attracted to the first magnet in the battery pack receiver and thereby hold the battery pack to the battery pack receiver.

In accordance with further aspect of the present disclosure, the battery pack is configured to cooperate with the battery pack receiver to form a handle at the proximal end of the barrel.

In accordance with still yet another aspect of the present disclosure, the light source comprises a ring array of LEDs. Ideally, the control circuit is configured to electrically couple the battery pack receiver to the light source for a period of time in response to detecting motion and then electrically uncouple the battery pack receiver from the light source in response to the period of time ending.

In accordance with another aspect of the present disclosure, a manual on-off switch is provided that is configured to override the control circuit and electrically couple and uncouple the battery pack from the light source in response to manual actuation of the on-off switch.

In accordance with yet another aspect of the present disclosure, the control circuit is configured to cause the light source to blink when a charge in the battery pack reaches a level of discharge.

According to a further aspect of the present disclosure, a kit is presented that includes a syringe having a light source mounted at a distal end of the syringe, the syringe having an electrical circuit configured to detect motion of the syringe and to illuminate the light source in response to the syringe moving; a battery pack configured to be mountable on a syringe chassis; a battery charger configured to accept the battery and electrically couple to the battery; and a container for housing the syringe during a sterilization process. In a further aspect, the light source is removably attached to the syringe. In yet another aspect, the electrical circuit is configured to decouple the battery pack from the light source in response to the syringe ceasing to move, preferably with a delay of appropriate length.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or components or both associated with syringes, including but not limited to plungers, needles, and carpules and the like have not been shown or described in order to avoid unnecessarily obscuring descriptions of the embodiments.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

Figure 1:
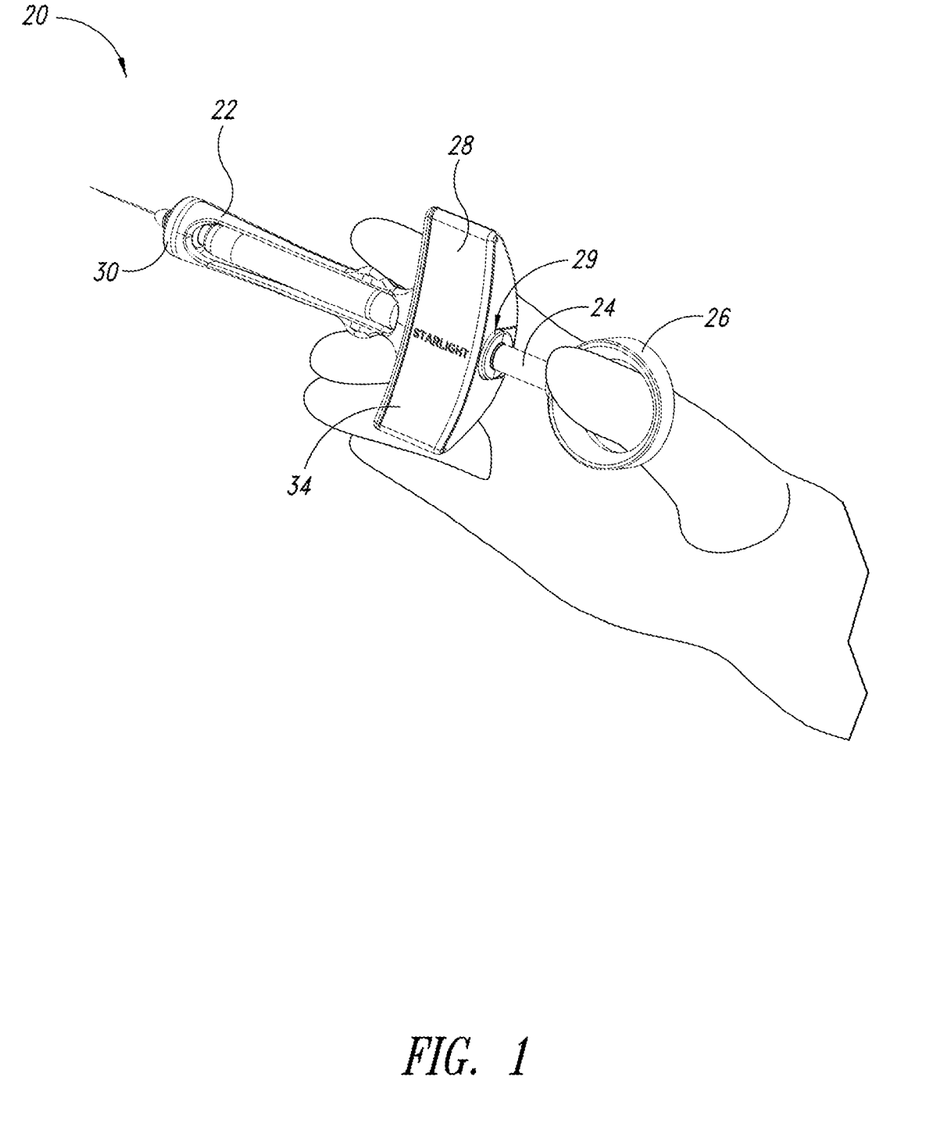
FIG. 1 is a pictorial illustration of an illuminated syringe formed in accordance with the present disclosure.
Figure 2:
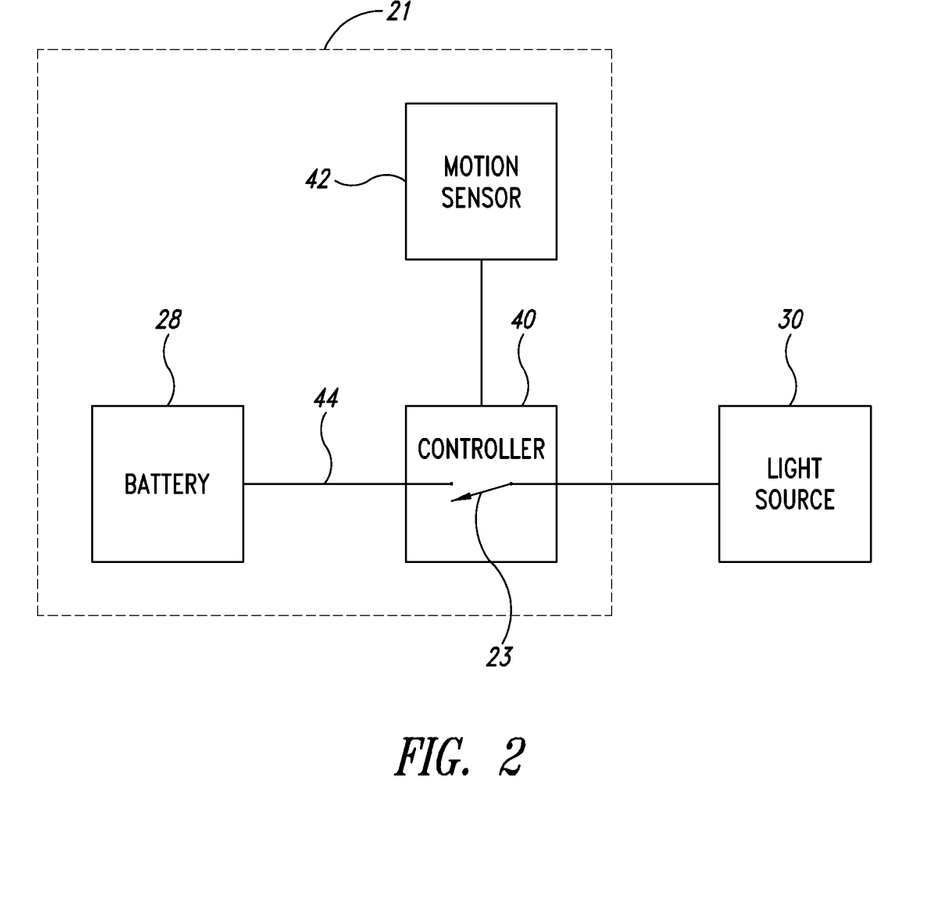
FIG. 2 is a block diagram of a control circuit of an illuminated syringe according to the present invention.

FIG. 1 shows an illuminated syringe 20 formed in accordance with one aspect of the present disclosure. The illuminated syringe 20 generally includes a shaft body or barrel 22 having a proximal end and a distal end. A plunger 24 is slidably mounted in a proximal end of the shaft body 22. A thumb ring 26 on the proximal end of the plunger 24 enables control of plunger 26 movement in the barrel or shaft body 22. At the proximal end of the shaft body 22 is a battery pack 28 removably coupled to a battery pack receiver 29. A light source 30 is electrically coupled to the battery pack receiver 29 and is mounted on a distal end of the shaft body 22 as described more fully below. A control circuit in the form of a controller 40 is associated with the light source 30 (shown in FIG. 2 schematically).

A hilt 34 is provided on the proximal end of the shaft body 22, and it is distal to the battery pack 28. In accordance with one aspect of the present disclosure, the battery pack receiver 29 forms a portion of or all of the hilt 34.

Syringes and their uses are common in medical fields and will not be described in detail here. Briefly, a carpule is inserted into the syringe 20, which is then punctured and delivered by a user depressing the plunger 24 using the thumb ring 26. A medication, generally a local anesthetic, is then injected into an injection site on the patient via a needle attached to the distal end of the syringe 20.

The illuminated syringe 20 uses the light source 30 to illuminate an injection site to facilitate injections in dark or hard to see spaces. Correct placement of the needle tip at the injection site can be critical in administering a local anesthetic to patients. Particularly in the dental field, it can be difficult to see an injection site in a patient's mouth because of the limited opening of the mouth and shadows created by the practitioner's head and hand and the syringe as well as the patient's oral structures, such as the cheeks and tongue. The light source 30 is placed at the distal end of the illuminated syringe 20, thus illuminating the injection site without objects between the light source 30 and the injection site.

The light source 30 is preferably integrated into the illuminated syringe 20. In one embodiment, the light source 30 comprises a plurality of LED lights arranged in a ring array and housed in an acrylic or acrylic-and-metal disc-shaped housing that is permanently or semi-permanently mounted on the distal end of the shaft body 22 with the LEDs facing along a longitudinal axis of the shaft body 22. One example of an LED that may be used in the LED array is the Citizen Electronics CLL600. In alternate embodiments, the light source could be made of any lights that are suitable for use with the illuminated syringe 20. The light source 30 is preferably housed in acrylic or an acrylic-and-metal housing in order to withstand the high heat used in the sterilization process. Alternatively, the light source 30 may be removably attached to allow a user to retrofit a standard syringe with the light source 30. In this design, the light source 30 could be housed in a heat-resistant material such as acrylic, or it may be housed in a non-heat resistant material if sterilization of the removable light source is not necessary.

The light source 30 is preferably located such that the light is directed primarily toward the injection site and circumferentially around the site while avoiding the emission of light back towards a user's eyes and interfering with the user's vision. For example, the light source will illuminate the injection site when the needle is oriented straight forward or at an angle of about 80 degrees or 70 degrees or even less than 70 degrees in some situations. The light source 30 may be configured to reflect or emit some amount of light into the shaft body 22 to illuminate the carpule, thus enabling the user to see the amount of medication in the carpule. Regardless of the design, it is important that light is prevented from shining back into the practitioner's eyes during the injection procedure.

In an alternative design, the light source 30 may be located along the shaft body 22. This may be implemented in addition to a light source 30 at the distal end of the syringe 20 or instead of the light source at the distal end. A light source 30 along the shaft body 22 would be directed toward the distal end of the illuminated syringe 20.

The illuminated syringe 20 also has a removable and rechargeable battery pack 28 that powers the light source 30. The battery within the battery pack 28 preferably has a voltage and amperage that are high enough to power all of the LEDs in the light source 30, while still being small enough to not obstruct use of the illuminated syringe 20. One example of a battery that may be used in the battery pack 28 is the CoinPower Varta. The battery pack 28 is preferably configured to be removable from the illuminated syringe 20 and rechargeable. As such, a user may have multiple battery packs 30 available for use, and therefore may charge one battery pack 28 while another battery pack 28 is being used. Removable battery packs 28 are also desired because the battery located inside the battery pack 28 may fail when introduced to the high temperatures of the sterilization process, and therefore it is advantageous to remove the battery pack 28 before sterilizing the illuminated syringe 20. In a preferred embodiment, the battery pack 28 is located on the proximal end of the shaft body 22. As shown in FIG. 1, this location allows the battery pack 28 to combine with the hilt 34 for the syringe to provide a resting place for the user's fingers while depressing the plunger 24. This also incorporates the proper weight and balance for the syringe 20 in the user's hand. Proper weighting so that the balance point of the syringe 20 is centrally located with respect to the user's hand provides for easier manipulation and more accurate placement of the needle in the patient's mouth.

The illuminated syringe 20 also includes a control circuit 21 that couples the battery pack 28 to the light source 30. The control circuit 21 detects motion of the illuminated syringe, such as when in it is picked up, and activates the light source 30 upon sensing this motion. In one embodiment, the control circuit 21 maintains illumination of the light source 30 for a fixed amount of time after sensing motion before shutting off the light source 30. Motion sensing allows the injection site to be illuminated before the practitioner begins the injection process. It also eliminates the need to slide or flip a switch, allowing the practitioner to safely perform the injection procedure without distraction. Automatically shutting off the light source after a fixed amount of time allows the practitioner to safely perform other tasks and ensures that the battery charge is preserved. In an alternative embodiment, the control circuit 21 may activate the light source 30 only while it senses motion, and shut the light source off when the motion stops, or for a fixed amount of time after motion starts or after motion stops.

The amount of time the light remains illuminated after motion starts or after motion stops can vary depending on the procedure. In some cases, the light source 30 will remain illuminated for a fixed period of time ranging from about 1 second to 120 seconds, or from about 5 seconds to and including about 90 seconds. Alternatively, the range could be from about 15 seconds to and including about 75 second or in the range from about 30 seconds to and including about 60 seconds. The control circuit 21 may be configured to enable a user to manually select the illumination time for the light source 30, either from the start of motion or from the cessation of motion. The control circuit 21 may also include, in addition to the motion activation circuit, a manual on/off circuit or switch that can be used to keep the light on or off regardless of the motion of the syringe or amount of time that the syringe is used. This manual switching may be controlled with the fingers or by voice command or other means that enables the practitioner to maintain control of the syringe and without having to use their fingers or hand to activate and deactivate the switch.

FIG. 2 shows a block diagram of the control circuit 21 of the illuminated syringe 20. The control circuit has a controller 40, a motion sensor 42, and a battery connector 44, and is coupled to the light source 30. The controller 40 is any processor capable of input, output, and logical processes, such as a microprocessor, multiplexer or logic gate. The battery connector 44 is a metallic connection that is located on the shaft body 22 where the battery pack 28 makes contact with the shaft body 22. The battery pack 28 has a matching metallic connection that makes electrical contact with the battery connector 44 when the battery pack is placed onto the shaft body 22.

The motion sensor 42 is preferably an accelerometer, but may be any sensor capable of detecting motion. The motion sensor is coupled to the controller 40, where a signal produced by the motion sensor 42 is processed. The controller 40 couples the battery pack 28 to the light source when the motion sensor 42 detects motion. In a preferred embodiment, the controller 40 begins a timer when the motion sensor 42 senses motion, and the battery and light source 30 remain coupled for the duration of the timer. In this embodiment, the light source will shut off automatically when the timer expires. In other embodiments, the controller 40 may not initiate the timer until it stops detecting motion or may not utilize a timer, and instead will couple the light source 30 based solely on the motion sensor 42 output.

The control circuit 21 may also contain a manually controlled on/off switch (not shown) as described above that is configured to override the motion sensor circuit and enable manual control of the light source 30. The on/off switch may comprise a rheostat to facilitate adjustment in the light intensity from the light source 30. The rheostat can be in the form of a slider switch, a rotary dial, or a thumb roller to facilitate one-handed operation.

In another aspect of the present disclosure, the controller 40 will couple the light source 30 and battery pack 28 when the battery pack has a low charge to illuminate the light source 30 as an alert that the battery is low. Preferably, the controller 40 will couple and decouple the battery pack 28 and light source 30 in succession in order to cause the light source 30 to blink to let the user know that the battery pack 28 needs to be recharged.

Figure 3:
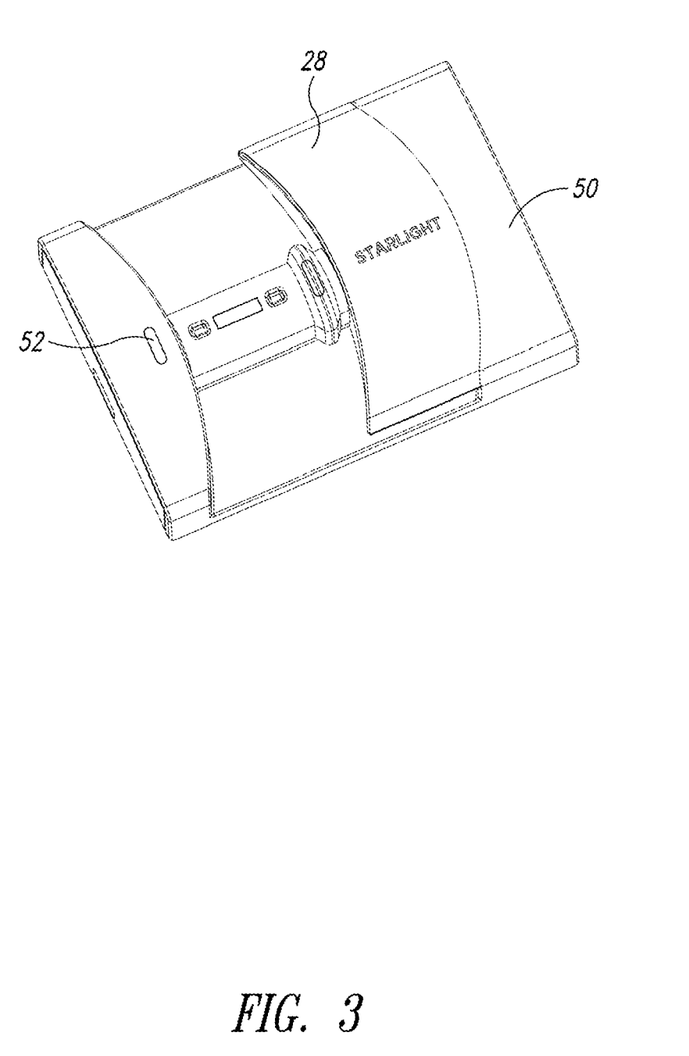
FIG. 3 is a battery pack and battery pack charger for use with the illuminated syringe of FIG. 1 according to the present disclosure.

FIG. 3 shows the battery pack 28 and an associated battery pack charger 50. The battery pack charger 50 is sized to receive the battery pack 28 securely. The charger 50 generally uses a standard wall outlet plug to power the charger, but may use other power connections such as USB. The charger has connectors that are sized and positioned to electrically connect with the connectors on the battery pack 28 to provide power to the battery pack 28. The battery pack 28 is removed from the illuminated syringe 20 so that it may be placed into the battery pack charger 50 while the illuminated syringe 20 is still being used. The charger 50 may contain one or more lights 52, preferably LEDs, to visually indicate when the battery pack 28 is charging and when the battery pack 28 is fully charged.

In accordance with one aspect of the present disclosure, the light source can be either a white light or another color of light or a combination of white and other color lights to achieve different lighting effects and to accommodate different conditions at the injection site. In addition to the foregoing, a light may also be used that aids in detecting cancer or that aids in curing composites. Thus various combinations of lights may be incorporated into the syringe in accordance with the present disclosure.

Figure 4:
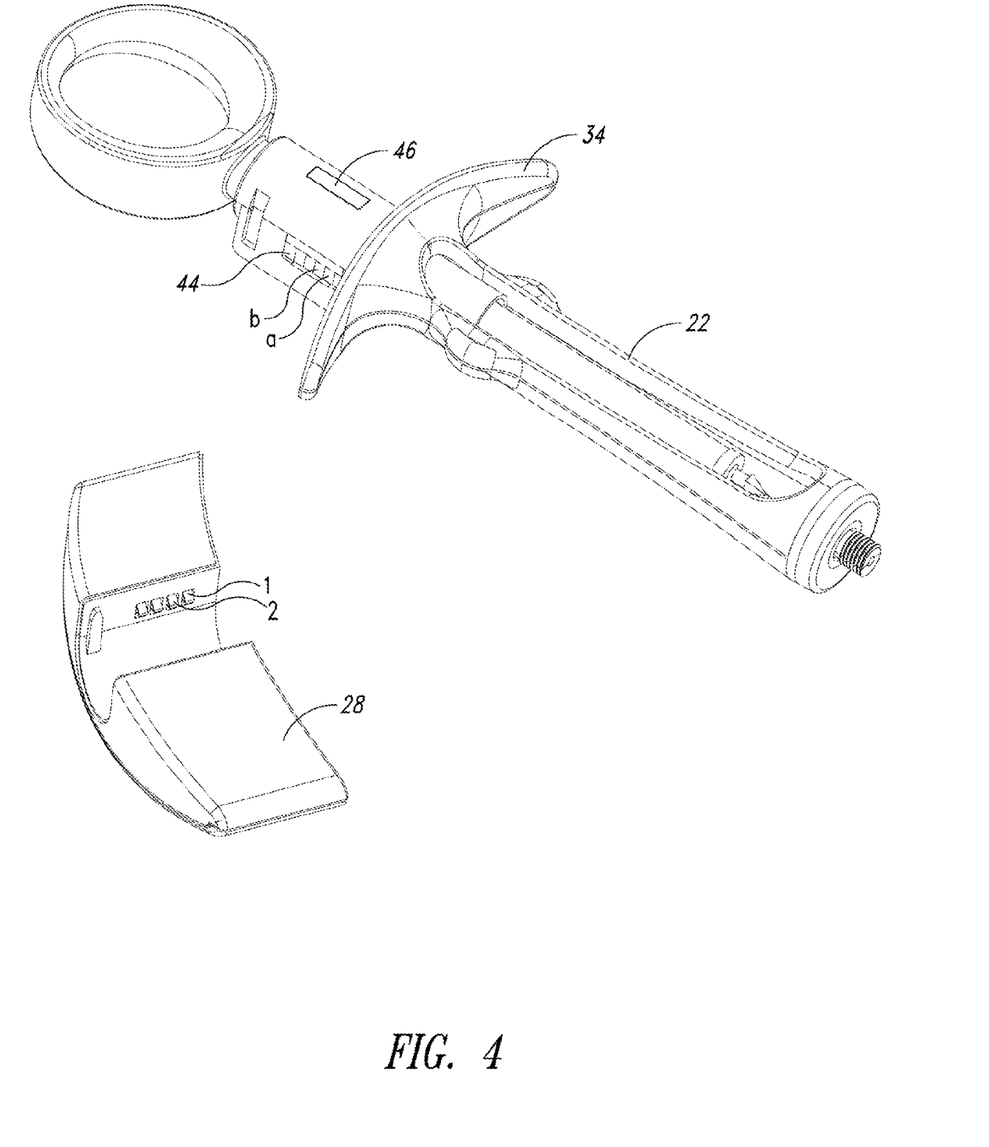
FIG. 4 is an illuminated syringe with a battery pack removed according to the present disclosure.
Figure 5:
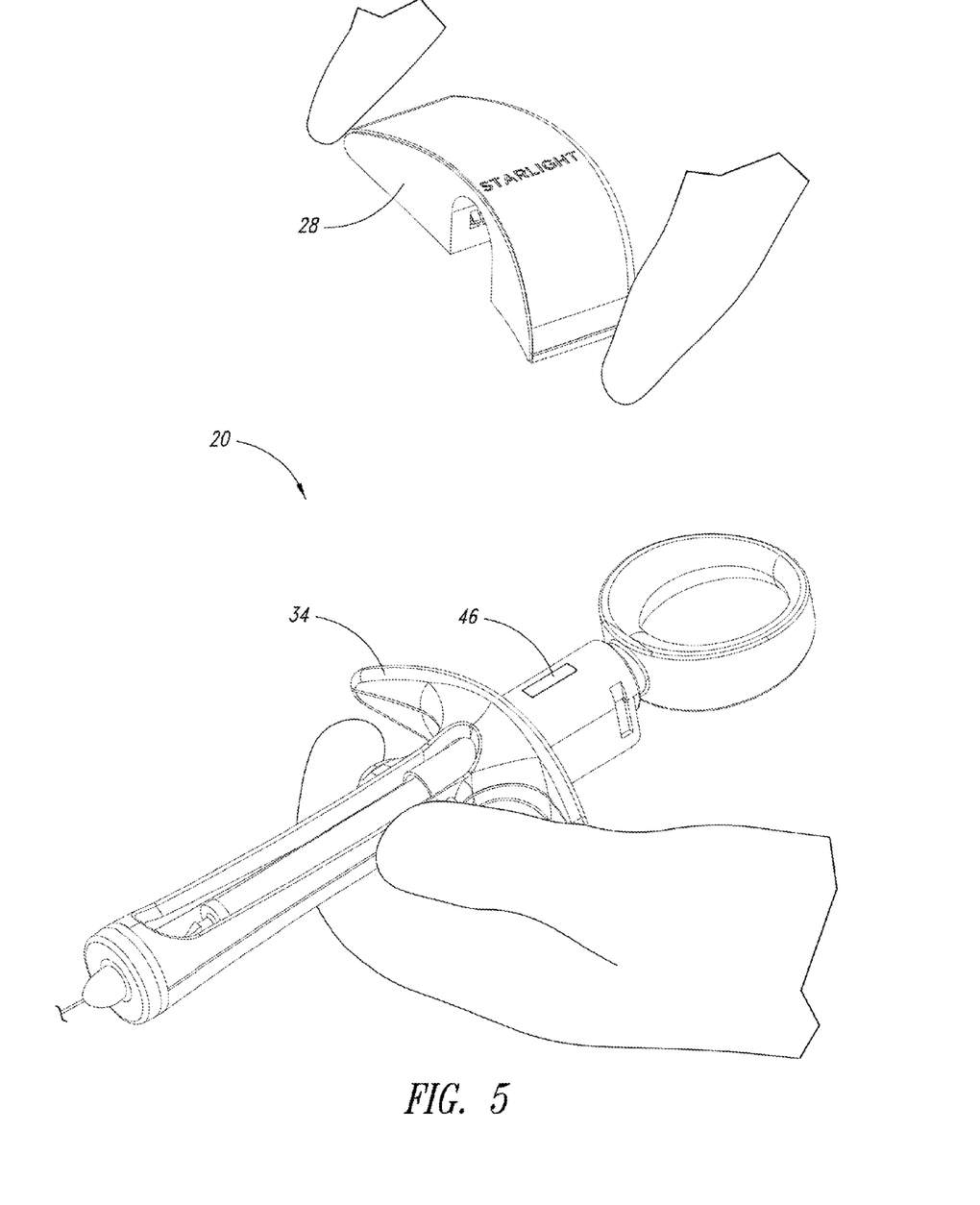
FIG. 5 is another view of the illuminated syringe with the battery pack removed of FIG. 4.

FIGS. 4-5 show the illuminated syringe 20 with the associated battery pack 28 removed. The battery pack 28 is formed with an indentation that is sized to fit around the hilt of the syringe. The syringe 20 has the hilt 34 formed onto the syringe to allow the syringe to be used even when the battery pack 28 is not attached. The battery pack 28 is preferably held to the illuminated syringe 20 with a series of magnets 46 or another attractive force. Holding the battery pack 28 magnetically to the battery pack receiver with either one set of magnets and a magnetically attracted piece of metal, or mutually attracted pair of magnets, one in the battery pack 29 and the other in the battery pack receiver 29, allows a user to handle the syringe and depress the plunger 24 without causing the battery pack to unintentionally become dislodged. In a preferred embodiment, the battery pack is held on with a force of at least 0.40 lbs., but may be held on with more or less force in other embodiments.

The controller 40 is preferably formed inside a structure associated with the battery pack receiver 29 or the hilt 34. However, it may be formed as a component of the battery pack itself.

In accordance with a further aspect of the present disclosure, mechanical means may be used to retain the battery pack on the syringe, such as clips, detents, latches, straps, and other known mechanical means. The mechanical means may be instead of or in combination with the magnetic holding.

Figure 6:
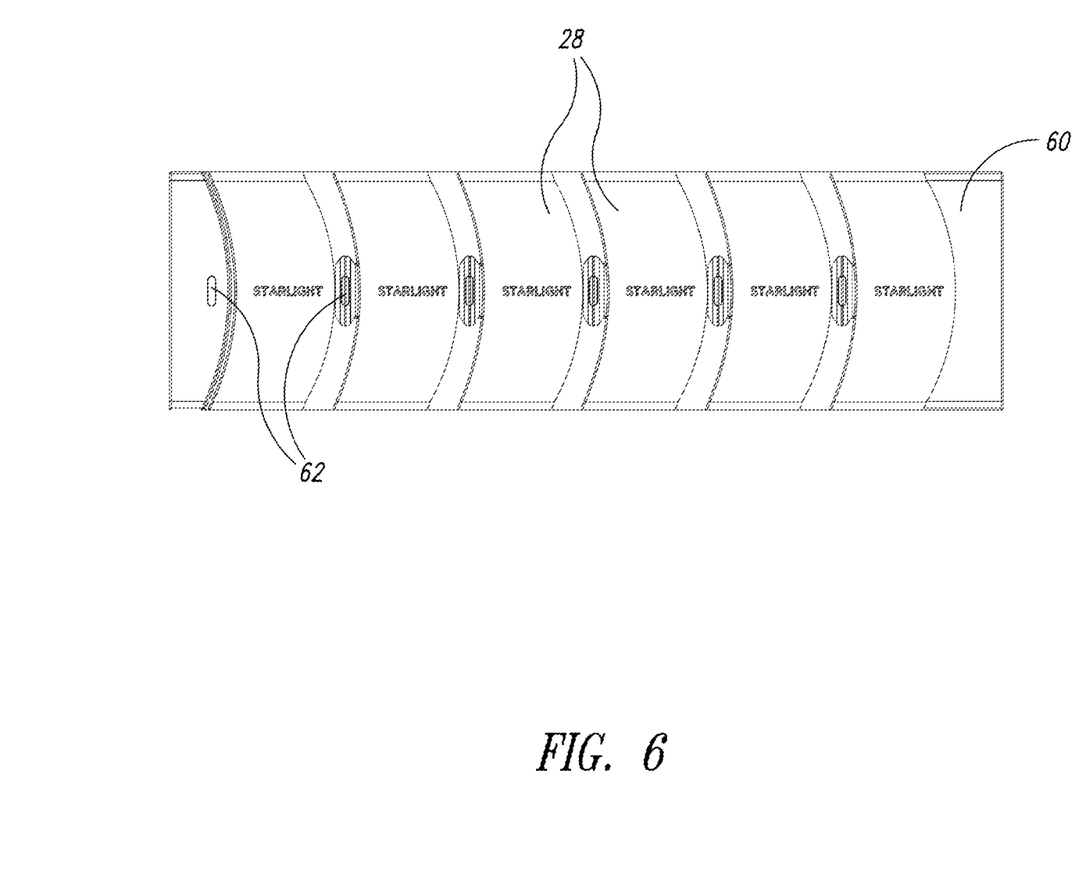
FIG. 6 is a plurality of battery packs and battery pack charger according to the present disclosure.

FIG. 6 shows an embodiment of a multi-battery pack charger 60 with a plurality of battery packs 28. The multi-battery pack charger 60 is configured to charge several battery packs 28 at the same time to allow a user to have a plurality of back-up battery packs or battery packs for multiple syringes. The multi-battery pack charger 60 preferably has a plurality of lights 62 that indicate the state of charge, such as when the battery packs 28 are charging and when they are fully charged. The multi-battery pack charger 60 allows a user to charge several battery packs 28 at the same time without requiring several battery pack chargers 50, which would take up a large amount of space and several electrical outlets.

Figure 7:
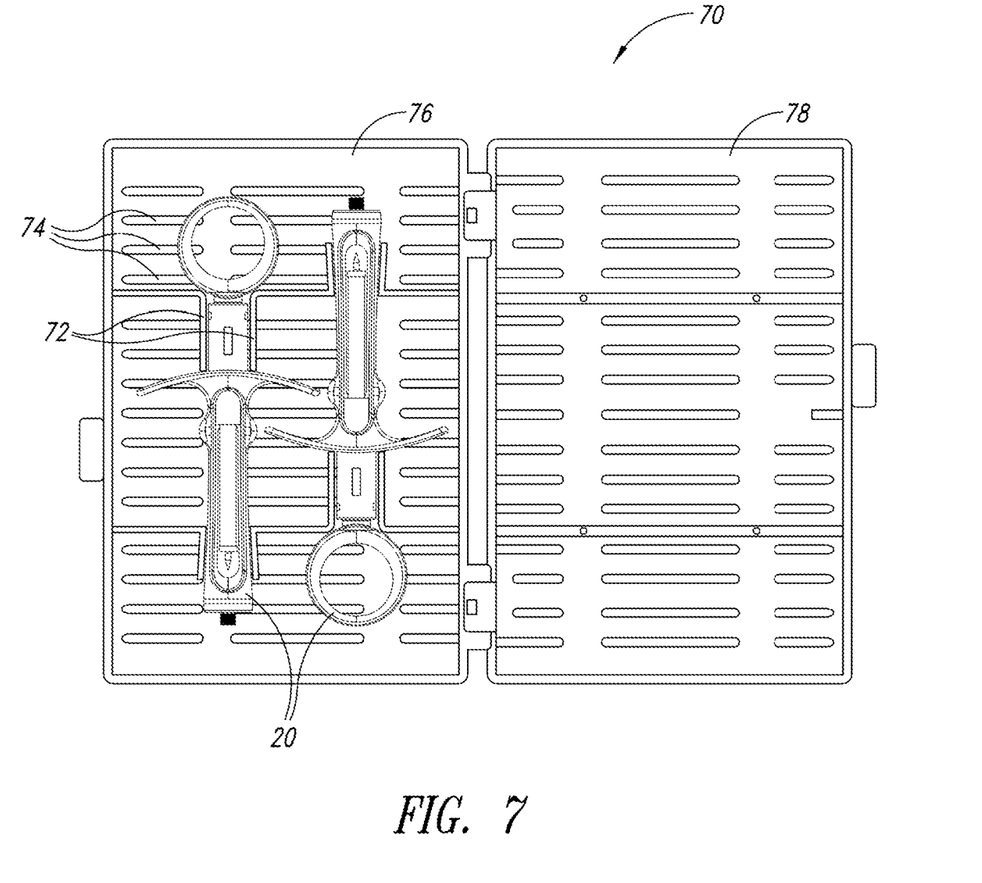
FIG. 7 is a top view of a custom cassette or tray for holding the syringe of FIG. 1 in an autoclave.

FIG. 7 shows a container or tray in the form of a cassette 70 that houses the illuminated syringe 20 during a sterilization process. Sterilization is an essential part of medical procedures, and the illuminated syringe 20 will require sterilization at various times before and after use. The cassette 70 is preferably designed for use with an autoclave process, but may also be used for other sterilization processes, such as chemical sterilization. The cassette 70 is configured to house at least one illuminated syringe 20, but preferably holds two illuminated syringes 20. The cassette 70 has a base 76 and a lid 78.

The lid 78 is hinged so that it may be opened for a user to access the syringes located on the base 76. The base 76 has clips 72 to hold the illuminated syringes in place during the sterilization process. The cassette 70 also has a number of slots 74 along the walls of the base 76 and lid 78 of the container to allow for the heated steam of an autoclave to penetrate the cassette 70 to fully sterilize the illuminated syringes 20.

In accordance with another aspect of the present disclosure, the cassette 70 is designed to prevent the syringe from being inserted into the slot 74 with the battery pack mounted on the syringe. The slot 74 is designed to prevent the battery pack from being inserted therein while allowing the syringe body to slide into the slot. This design forces the battery pack to disengage from the syringe body when the syringe body slides into the slot. The disengaged battery pack will prevent the cover of the cassette 70 from closing until the disengaged battery pack is removed from the interior of the cassette 70.

Figure 8:
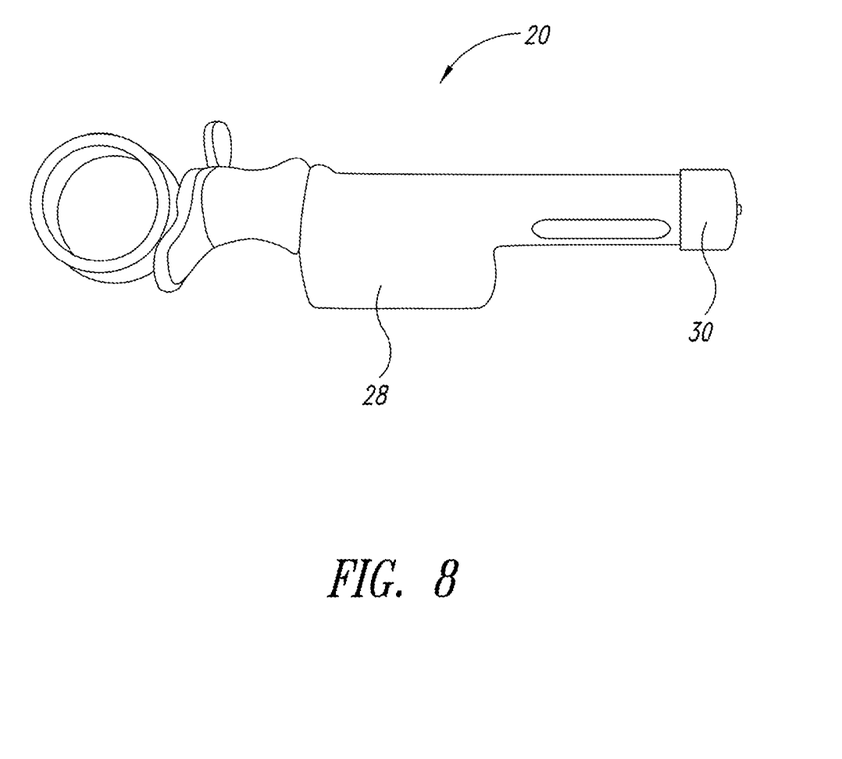
FIG. 8 is an illuminated syringe with a battery pack adjacent a shaft body formed in accordance with another aspect of the present disclosure.

FIG. 8 shows an alternative embodiment of an illuminated syringe 80. In this embodiment, the battery pack 82 is located adjacent the shaft of the illuminated syringe 80. This design can be used with a permanent light source 30 or a removable light source 30. In a permanent light source configuration, the battery pack 82, light source 30, and control circuit 21 will operate in the same fashion as described above, with only the location of the battery pack being changed. In an embodiment where the light source 30 is removable, the battery pack 82, control circuit 21, and light source 30 will preferably be housed as one package that may be fitted over the shaft body 22 of a standard syringe. Housing all the battery pack, circuitry and light source in one package allows for easy attachment and removal of the light source 30 to the syringe without requiring circuitry located in the syringe. The combined unit of the removable light source 30, battery pack 28, and control circuit 21 is generally configured to slide over the shaft of a standard syringe, but may be attached in any suitable manner.

Figure 9:
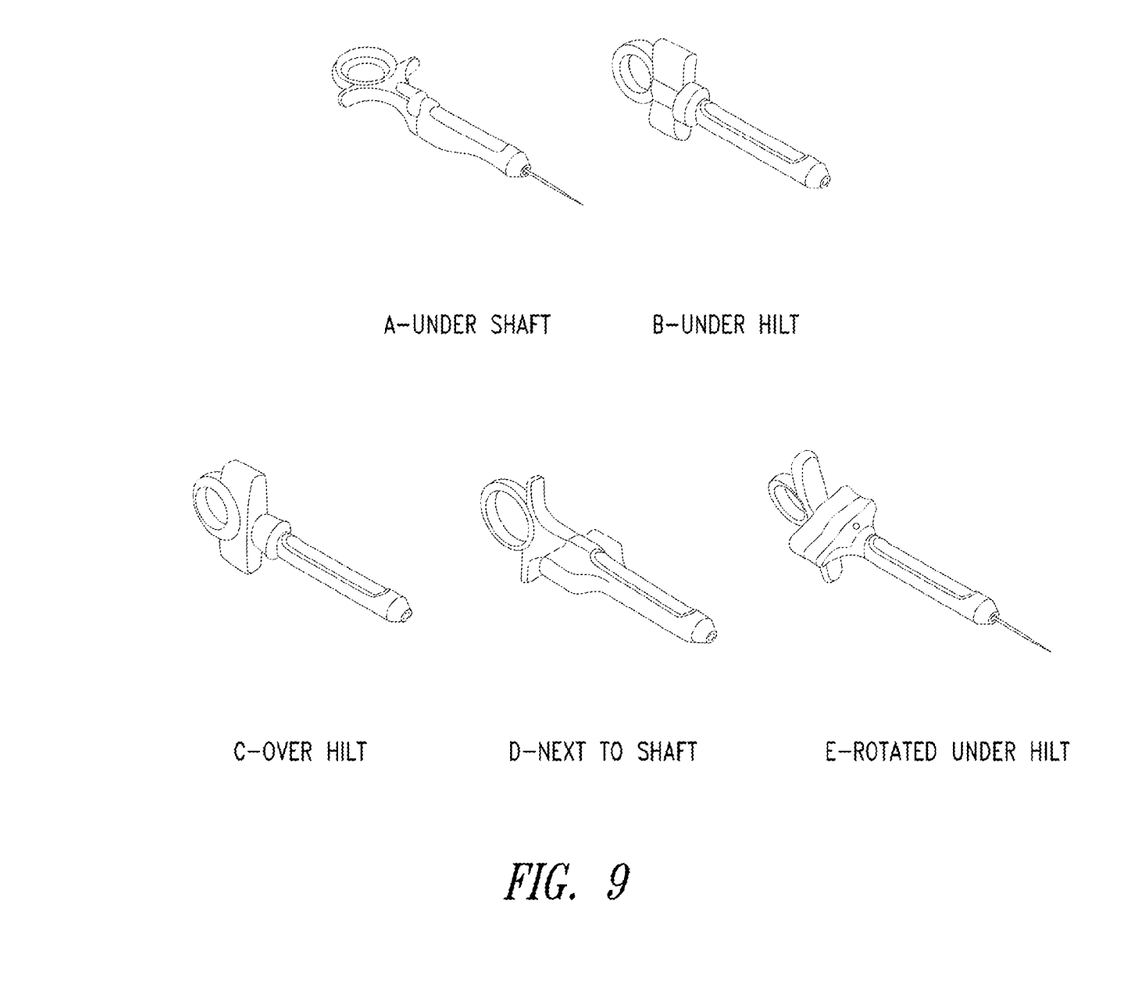
FIG. 9 is a plurality of alternative designs of an illuminated syringe and battery pack.

FIG. 9 shows several different design variations of the illuminated syringe wherein the battery pack is located in different positions. In these embodiments, the battery pack may be located in a variety of configurations near the hilt of the syringe or along the body shaft of the syringe.

Figure 10:
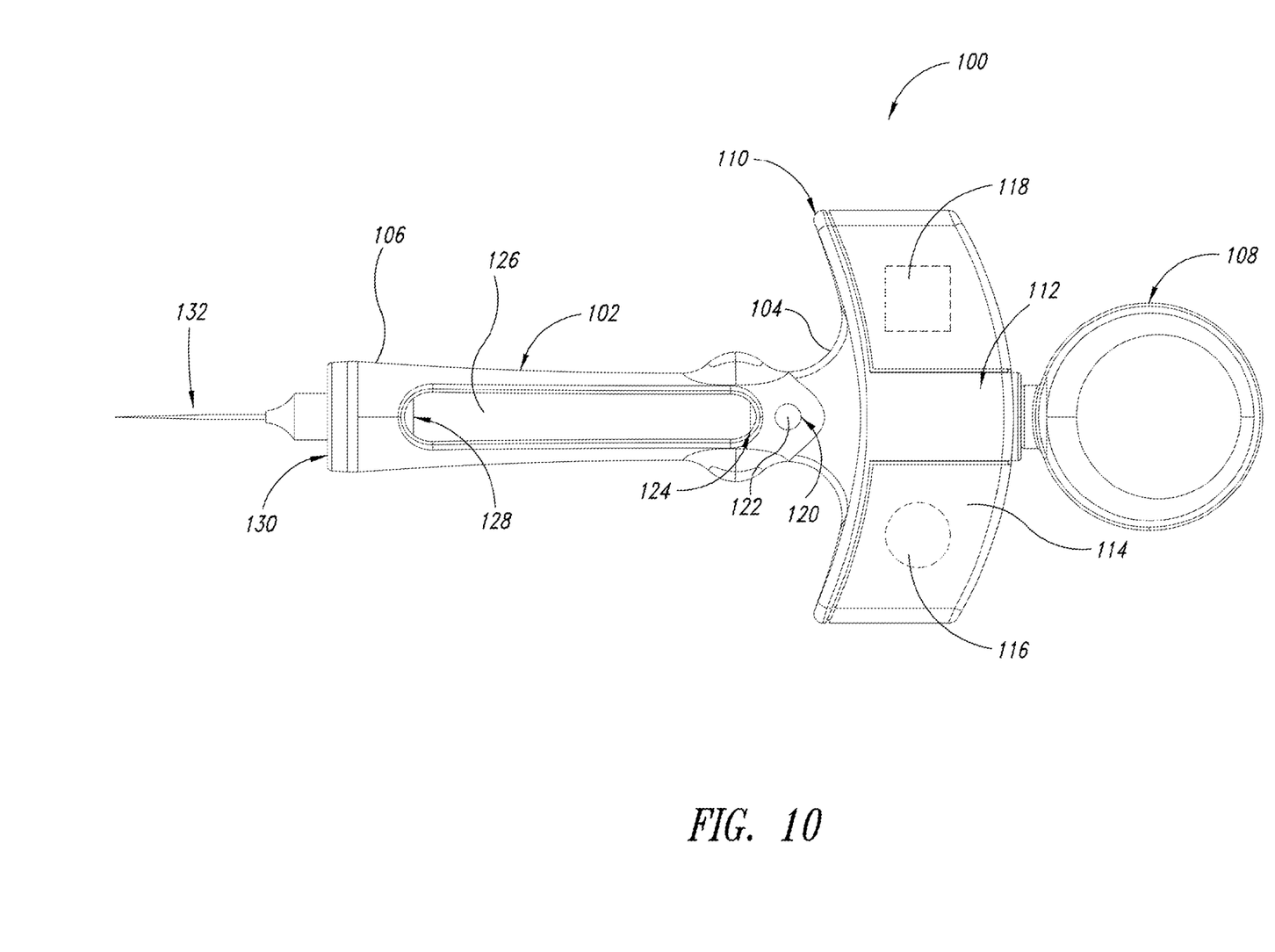
FIG. 10 is a top plan view of an alternative design for an illuminated syringe utilizing light pipes in accordance with the present disclosure.

Referring next to FIG. 10, shown therein is an alternative design of a syringe 100 having a barrel 102 with a proximal end 104 and distal end 106. A plunger (not shown) is mounted in the barrel 102 through the distal end 106 for slidable movement along a longitudinal axis of the barrel 102. A thumb ring 108 is provided at the proximal end of the plunger to enable one-handed actuation of the plunger. At the proximal end 104 of the barrel 102 is a hilt 110 having a battery pack receiver 112 formed thereon that is configured to receive a battery pack 114. The battery pack 114 includes a battery 116 and a circuit board 118.

In this version, a light source 120 is provided in the form of a high-powered LED light 122 mounted in the hilt 110. Mounted adjacent to the LED light 122 on the distal side is an optional lens 124 configured to collect and focus light from the LED light 122.

Formed on or in the barrel 102 is a single or multiple fiber optic light pipe 126 configured to convey light from the LED light 122 down the barrel 102 to the distal end 106 thereof. At the distal end 106 is a second optional lens 128 configured to collect and refocus the light. An optional diffuser or third lens 130 may be positioned distal to the second lens 128 for diffusing the light exiting the light pip 126. The light pipe 126 and lens 128 along with the diffuser 130 are configured to direct the line axially along the longitudinal axis of the barrel 102 and along the needle 132 projecting from the distal end 106 of the barrel 102. One or more of the features described in conjunction with the foregoing designs may be combined with this version.

Proper consideration has been given to weight distribution and balance about a center of gravity of the syringes described herein. As described above, the syringes include a built-in hilt that facilitates use when the battery pack is removed from the battery pack receiver. Hence, the designs presented herein facilitate several modes of operation.

Consideration has also been given to aesthetic appeal of the syringes. For this reason a number of ornamental features and cosmetics have been included in the various designs without explanation. These include without limitation, symmetry, balance, various radii of curvature of some features, size and position of various features relative to one another, and visually appealing presentation in the kit form. Such features are not critical or necessary to the function of the syringes and may be the subject of separate design patent protection.

Figure 11A:
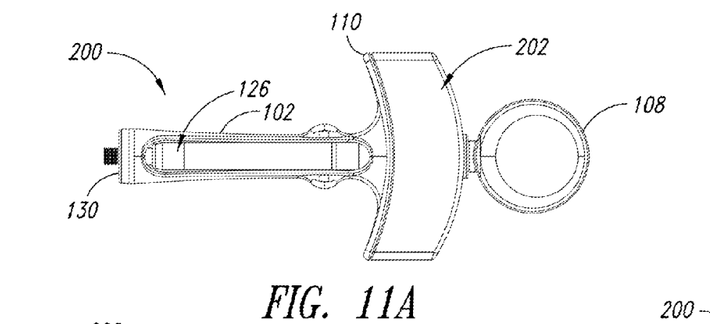
FIGS. 11A-11E illustrate another alternative design for an illuminated syringe formed in accordance with the present disclosure.
Figure 11B:
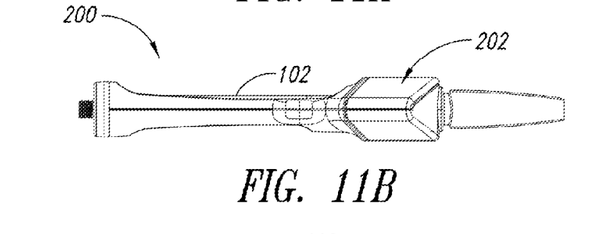
Figure 11C:
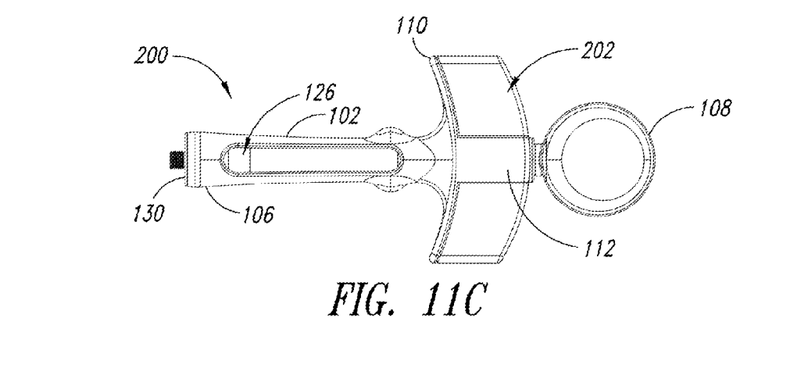
Figure 11D:
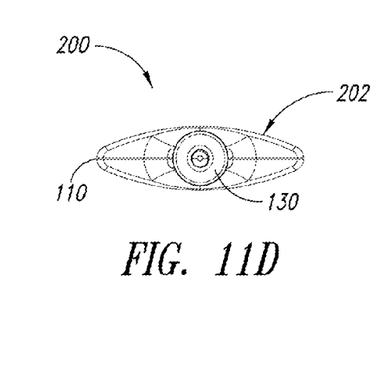
Figure 11E:
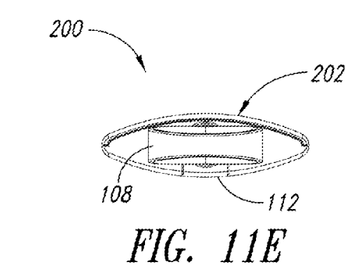

For example, FIGS. 11A-11E illustrate another embodiment of a syringe 200 formed in accordance with the present disclosure. Reference numbers from FIG. 10 are adopted here for the same elements. As can be seen here, the aesthetic appeal of this syringe 200 is much greater due to the design changes. These changes include without limitation the battery pack 202, which has a more symmetrical shape when viewed on end, as seen in FIGS. 11B, 11D, and 11E.

Figure 12:
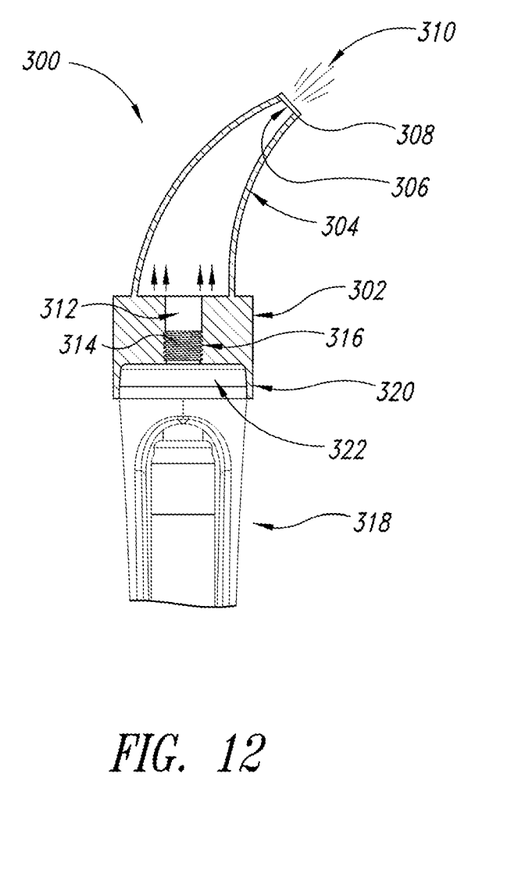
FIGS. 12 is a cross-sectional illustration of an alternative lighted removable syringe tip design formed in accordance with the present disclosure.

FIG. 12 illustrates a cross-sectional view of a removable syringe tip design in accordance with the present disclosure. As shown therein, the syringe tip 300 includes a cylindrical body 302 having a cone-shaped light pipe 304 extending from a distal end of the body 302. The light pipe 304 includes a lens 306 at the projecting end 308 to concentrate light 310 exiting the tip 300.

The tip body 302 has a longitudinal axial bore 312, at least a portion of which has internal threads 314 to enable the tip 300 to be threadably engaged with an existing male syringe threads 316 (usually used to twist on a needle hub) to lock the tip 300 into place on the LED end of the syringe 318. The body 302 also has a sleeve portion 320 extending past the terminal end of the body 302 that is configured to slip over the LED light 322 on the end of the syringe 318. Ideally the Tip 300 is made of opaque acrylic such that light from the LED 322 does not escape past or through the sleeve portion 320 and is directed through the light pipe 304 to the lens 306

As mentioned above, the present disclosure includes a kit having a syringe with a light source mounted at a distal end of the syringe, the syringe having an electrical circuit configured to detect motion of the syringe and to illuminate the light source in response to the syringe moving, a battery pack configured to be mountable on a syringe chassis, or alternatively on a plunger of the syringe, a battery charger configured to receive the battery and electrically couple to the battery and charge the battery, and a container for housing the syringe during a sterilization process.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus, comprising:
a sterilizable syringe having a barrel with a proximal end and a distal end and an integral hilt;
a plunger mounted in the barrel and longitudinally slidable through the proximal end of the barrel;
a light source integrally formed on the distal end of the barrel;
a battery pack receiver on the hilt and configured to be electrically coupled to the light source;
a battery pack configured to be removably mounted to the battery pack receiver by magnetic attraction between the battery pack and the battery pack receiver, the battery pack positioned on the hilt to centrally locate a weight balance point of the syringe; and
a control circuit and a motion sensor sealed inside the battery pack and configured to be electrically coupled to the battery pack receiver and the light source and configured to detect motion of the syringe and to electrically couple the battery pack receiver and the light source in response to detecting motion of the syringe, the syringe configured for use as a syringe when the battery pack is removed.

2. The apparatus of claim 1, comprising a first magnet in the battery pack receiver and a second magnet in the battery pack configured to be magnetically attracted to the first magnet in the battery pack receiver and thereby hold the battery pack to the battery pack receiver.

3. The apparatus of claim 1, wherein the battery pack is configured to cooperate with the battery pack receiver to form a handle at the proximal end of the barrel.

4. The apparatus of claim 1, wherein the light source comprises a ring array of LEDs configured to primarily illuminate circumferentially around an injection site while avoiding emission of light back to a user's eyes and to partially illuminate a carpule on the syringe to enable visual checking of the amount of contents in the carpule.

5. The apparatus of claim 1, wherein the control circuit is configured to cause the light source to blink when a charge in the battery pack reaches a level of discharge.

6. The apparatus of claim 1, wherein the control circuit is configured to electrically couple the battery pack receiver to the light source for a period of time in response to detecting motion and then electrically uncouple the battery pack receiver from the light source in response to the period of time ending.

7. The apparatus of claim 6, wherein the control circuit includes a manual on-off switch located on the battery pack and configured to override the control circuit and electrically couple and uncouple the battery pack from the light source.

8. A syringe, comprising:
a hilt;
a barrel extending from the hilt and having a proximal end and a distal end;
a light source integral with the distal end of the barrel, the light source comprising a disc-shaped array of light emitters disposed circumferentially around a longitudinal axis of the barrel and configured to illuminate circumferentially an area around an injection site while avoiding the emission of light back to a user's eyes and to partially illuminate a carpule on the barrel;
a battery pack receiver coupled to the light emitters;
a battery pack configured to be held in the battery pack receiver and to centrally locate a weight balance point on the syringe;
a control circuit with a motion sensor inside the battery pack and configured to electrically couple a battery in the battery pack to the light emitters and configured to detect motion of the syringe and to electrically couple the battery pack receiver to the light emitters in response to detecting motion of the syringe.

9. The syringe of claim 8, wherein the disc-shaped array of light emitters comprise LED lights arranged circumferentially around a longitudinal axis of the barrel.

10. The syringe of claim 8, comprising:
a first magnet in the battery pack receiver; and
a second magnet in the battery pack configured to be magnetically attracted to the first magnet in the battery pack receiver and thereby hold the battery pack to the battery pack receiver.

11. The syringe of claim 8, wherein the control circuit is configured to electrically couple the battery pack receiver to the light emitters for a period of time in response to detecting motion of the syringe and then electrically uncouple the battery pack receiver from the light emitters in response to expiration of the period of time.

12. The syringe of claim 11 comprising a manually operable on-off switch in the control circuit configured to override the motion detection and enable manual control of operation of the light emitters.

13. The syringe of claim 11, wherein the light emitters comprise a plurality of optical fibers in the hilt and configured to provide light at the distal end of the barrel; and
a light source optically coupled to the plurality of optical fibers and electrically coupled to the battery pack.

14. The syringe of claim 13 comprising a manually operable on-off switch on the battery pack and electrically coupled to the control circuit and configured to override the motion detection and enable manual control of operation of the light source.

15. A kit, comprising:
- a syringe having a light source integrally formed on a distal end of the syringe, the syringe having an electrical circuit with a motion sensor formed inside the syringe and configured to detect motion of the syringe and to illuminate the light source in response to the syringe moving;
- a battery pack configured to be mountable on a plunger of the syringe;
- a battery charger configured to receive the battery pack and electrically couple to the battery pack and charge the battery pack; and
- a cassette that is configured to house the syringe during a sterilization process while preventing the inclusion of the battery pack with the syringe.

16. The kit of claim 15, wherein the control circuit includes a manually actuatable switch configured to override the control circuit and electrically couple and uncouple the light source from the battery pack.

17. The kit of claim 15, wherein the electrical circuit is configured to electrically decouple the battery pack from the light source after a pre-determined period of time after detecting motion.

* * * * *